United States Patent
Erdelmeier et al.

(10) Patent No.: US 6,280,736 B1
(45) Date of Patent: *Aug. 28, 2001

(54) STABLE EXTRACT OF *HYPERICUM PERFORATUM L.,* PROCESS FOR PREPARING THE SAME AND PHARMACEUTICAL COMPOSITIONS

(75) Inventors: Clemens Erdelmeier, Karlsruhe; Eckhart Grethlein, Pfinztal; Friedrich Lang, Hagenbach; Rainer Oschmann, Landau; Karl-Heinz Stumpf, Karlsruhe, all of (DE)

(73) Assignee: Ur. Willmar Schwabe GmbH & Co,, Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,939
(22) PCT Filed: Sep. 27, 1996
(86) PCT No.: PCT/DE96/01876
§ 371 Date: May 14, 1998
§ 102(e) Date: May 14, 1998
(87) PCT Pub. No.: WO97/13489
PCT Pub. Date: Apr. 17, 1997

(30) Foreign Application Priority Data

Sep. 29, 1995 (DE) ............................. 195 36 496
Mar. 22, 1996 (DE) ............................. 196 11 374
May 14, 1996 (DE) ............................. 196 19 512

(51) Int. Cl.$^7$ .................................................. A61K 35/78
(52) U.S. Cl. ........................................................ 424/195.1
(58) Field of Search .......................................... 424/195.1

(56) References Cited

U.S. PATENT DOCUMENTS

| | | | |
|---|---|---|---|
| 4,178,372 | 12/1979 | Coats ........................... | 424/195.1 |
| 4,446,131 | 5/1984 | Maughanl ..................... | 424/195.1 |
| 5,401,502 | * 3/1995 | Wunderlich et al. .......... | 424/195.1 |

FOREIGN PATENT DOCUMENTS

| | | |
|---|---|---|
| 876 309 | 3/1953 | (DE). |
| 36 41 220 A1 | 6/1988 | (DE). |
| 41 31 313 A1 | 3/1993 | (DE). |
| 0 051 789 A2 | 5/1982 | (EP). |
| 0 599 307 A1 | 6/1994 | (EP). |
| 2101888 | * 1/1983 | (GB). |
| 79428 | * 2/1983 | (RO). |

OTHER PUBLICATIONS

Maisenbacher, P. et al., Planta Medica, vol. 58(4), p. 351–354, 1992.*

*Pharm. Stoffliste, properties and use of acorbic acid*, pp. 314–315.

"Medicinal Plants in the Soviet Union," *Reports of the Institutes for East Europe at the Free University of Berlin*, vol. 44, pp. 134–138, Berlin 1966, (a English translation of the section titled "Inhalfstoffe" on p. 134).

Section 2.3.6 "Other ingredients" of p. 15 of the Maisonbacher Ph.D. thesis.

"Lexikon der Hilfsstoffe", which carries the header "D3 EPI".

Römpp Chemie Lexikon (Römpp Chemical Dictionary), which carries the header "D3 EPIII/IV".

H. Finzelberg's Nachfolger GmbH & Co KG, Batch documentation (batch 1565931, article 0155610) for oleum hyperici olive base oil (printout dated Apr. 20, 1999) English Translation.

H. Finzelberg's Nachfolger GmbH & Co KG, internal specification for preparation of Oleum mac. Hyperici e flor (parent extract) English Translation.

H. Finzelberg's Nachfolger GmbH & Co KG, Results of Analysis 99–15 preparation of hypericum extracts with and without stablizers/test of hperforin stability. English Translation.

H. Finzelberg's Nachfolger GmbH & Co KG, Stability of Hperforin in Hypericum extracts according to example 2 of DE 196 19 512 (Apr. 14, 1999) English Translation.

H. Finzelberg's Nachfolger GmbH & Co KG validating report (excerpt) for Hypericum total extracts; extracting agent 60% EtOH (m/m) (Apr. 20, 1999) English Translation.

H. Finzelberg's Nachfolger GmbH & Co KG, Hyperforin contents in Finzelberg's Hypericum extracts–long–term values (Nov. 16, 1998) English Translation.

H. Finzelberg's Nachfolger GmbH & Co KG, Hyperforin contents in St. John's wort fresh plant $CO_2$ extracts (Apr. 16, 1999). English Translation.

H. Finzelberg's Nachfolger GnbH & Co KG, Preparation of various Hypericum extract according to example 1 of Schwabe's Patent No. EP 0 599 307 A1 (D4) as well as example 1 of DE 196 19 512 and subsequent stability testing (Aug. 23, 1999). English Translation.

H. Finzelberg's Nachfolger GmbH & Co KG GmbH & Co KG, Result of analysis No. 99–74, Preparation of Hypericum Extracts with and without stablizers/test of Hperforin stability. English Translation.

(List continued on next page.)

Primary Examiner—Jean C. Witz
(74) Attorney, Agent, or Firm—McDonnell Boehnen Hulbert & Berghoff; Steven J. Sarussi

(57) ABSTRACT

Disclosed is an improved extract of *Hypericum perforatum L.* (St. John's wort) containing Hyperforin, in which the Hyperforin is stabilized against decomposition or degradation by means of a stabilizer.

33 Claims, No Drawings

OTHER PUBLICATIONS

Gehrlicher GmbH & Co. KG, Stability ofHperforin (Table 1A). English Translation.
Gehrlicher GmbH & co. KG, Stability of Hyperforin (Table 1B).
Dr. Willmar Schwabe GmbH & Co., Stability of Hperforim at room temperature in stabilized and non–stabilized Hypericum Extracts (D31).
Dr.Willmar Schwabe GmbH & Co. Table1. Content and stility ofHyperforin in preparations of St. John's Wort (D32). German/English Translation.
Ullmann's Encyclopedia of Industrial Chemistry, vol. A 10, p. 288–289 (D4 EP IIIIV).
Dr. Willmar Schwabe GmbH & co., Comparison of Hperforin stability in non–stailized $CO_2$ extracts from fresh plant and drug (D 25).
"Red List" 1992, preparation No. 70 021 "Psychatrin Jossa".
An analysis Biocur Arzneimittel GmbH, of preparation No. 70 021 "Psychatrin Jossa" of the "Red List" 1992.
Renate Berghöfer, Dissertation Botanice, vol. 106, 1987.
Dissertation by Peter Maisenbacher "Untersuchungen zur Analytik von Johanniskrautöl [Studies on the analysis of St. John's wort oil]", Tübingen 1991, pp. 139–168.
Römpp Chemielexikon [Römpp's Chemical Dictionary], 9th edition, 1990, p. 910.
Data Base EPI Section Ch., 37th week 1983, Derwent Publications Ltd., London, GB; class B05, AN 83–762732 XP 002033079, & RO 79 428 A (Inter Med Coloranti Sintopharm), Feb. 28, 1983.
RP 79428, Translation.
R. Hänsel et al.: Drogen E–O [Drugs E–O], Springer–Verlag, Berlin 1993, vol. 5, pp. 474–495.
Invoice of Sep. 11, 1994 and "St. John's wort" specification from FLAVEX Naturextrakte GmbH.
Wohlfahrt, Wurm, Hänsel and Schmidt, Arch. Pharm. (Weinheim) 315, (1982), pp. 132–137 ("Der Abbau der Bittersäuren zum 2–Methyl–3–buten–2–ol, einem Hopfeninhaltsstoff mit Sedativ–hypnotischer Wirkung [The breakdown of bitter acids to 2–methyl–3–buten–2–ol, a constituent of hops with a sedative–hypnotic action]").
Täufel/Ternes/Tunger/Zobel, Lebensmittellexikon [Foodstuffs Dictionary], Behr's Verlag, Hamburg, 3rd edition, 1993, vol. 1, pp. 109–116.
Römpp Chemielexikon [Römpp's Chemical Dictionary], 9th edition, 1989–1992, vol. 1, pp. 265/266; vol. 2, p. 846 and vol. 6, pp. 4589/4590.
Stability of pure hyperforin with and without BHT.

* cited by examiner

STABLE EXTRACT OF *HYPERICUM PERFORATUM L.*, PROCESS FOR PREPARING THE SAME AND PHARMACEUTICAL COMPOSITIONS

It is proved by pharmacological and clinical trials that extracts of St. John's wort (extracts of Hypericum) can be successfully used in case of light to moderately severe depressions. The mild anti-depressive overall effect could not be exactly assigned to one or several components; cf J. Hölzl, S. Sattler and H. Schütt, Johanniskraut: Eine Alternative zu synthetischen Antidepressiva (St. Johns wort: an alternative to synthetic antidepressants), *Pharmazeutische Zeitung*, No. 46, 139. Jahrgang, 17. November 1994, pages 3959–3977. However, recently there are stronger hints that Hyperforin provides a considerable contribution to achieve effectiveness (EP-A-0 599 307).

The crude herbal drug consists of the aerial parts of *Hypericum perforatum L*. The components of *Hypericum perforatum L*. are among others Hypericin and Hyperforin; cf. J. Hölzl et al., see above.

The preparation of extracts of Hypericum with an enriched content of Hypericin is described in DE-PS- 1 569 849 as well as in S. Niesel and H. Schilcher in *Arch. Pharm*., Vol. 323 (1990), page 755.

From R. Berghöfer and J. Hölzl, *Deutsche Apothekerzeitung*, Vol. 126, No. 47 (1986) pages 2569–2573, it is known that Hyperforin in extracts from stored crude herbal drugs is already completely degraded after one week whilst it should be more stable in the extract of fresh plants. These authors assume that fresh plants contain a stabilizer for Hyperforin.

J. Hölzl et al., *Planta Med.*, Vol. 55 (1989) pages 601–602 report about Hypericum oil and assume a correlation between the concentration of Hypericin and the peroxide value. Hypericum oil products exposed to the sun light show different peroxide values. But according to J. Hölzl et al., there is no relation between the peroxide value and the concentration of Hypericin.

P. Maisenbacher and K.-A. Kovar report in *Planta Med.*, Vol. 58, (1992), pages 351 to 354 about the stability of Hypericum oil. This oil also contained Hyperforin which was degraded within a few weeks.

From EP-A- 0 599 307 (corresponding to DE-OS 4 239 959) extracts of Hypericum and processes for its preparation are known which contain as less as possible Hypericin and similar photosensitising compounds but nevertheless show the effectivity that was formerly thought to result from Hypericin. The effectivity can be explained by the presence of Hyperforin.

Furthermore, it is known to prepare Hypericum oil (oil of St. John's wort; Oleum hyperici) by extraction of crushed (mashed) fresh flowers of St. John's wort with a fatty oil such as olive oil, soya-bean oil, wheat germ oil or sunflower seed oil. Hypericum oil contains variable amounts of Hyperforin and is useful for the topical treatment of wounds, in particular burns and abrasion; cf. P. Maisenbacher and K.-A. Kovar, *Planta Med.*, Vol. 58 (1992), pages 351–354 and J. Hölzl, L. Demisch and S. Stock, *Planta Med.*, Vol. 55 (1989), pages 601–602.

As well in the drug as in conventional extracts of Hypericum the content of Hyperforin decreases dramatically until the disappearance of the substance within a few months on conventional storage; cf Ph.D. thesis of P. Maisenbacher, Tübingen 1991 and the Ph.D. thesis of R. Berghöfer, Marburg /L. 1987. In earlier experiments with oily extracts of Hypericum the stability of compositions containing Hyperforin could only be improved in a better way by storage under Argon; cf. Ph.D. thesis of P. Maisenbacher, see above. A stabilisation with anti-oxidants such as butylhydroxytoluene (BHT) and butylhydroxyanisole (BHA) was not achieved in these extracts. Moreover, conventional anti-oxidants such as Oxynex LM and Oxynex 2004 do also not improve the stability. In case of Hypericum oil the best stability is achieved (according to P. Maisenbacher's Ph.D. thesis) by use of octyldodecanol (Eutanol G) as an extraction agent.; cf see P. Maisenbacher's Ph.D. thesis, pages 151–154.

Extracts of Hypericum containing Hyperforin can be prepared with pharmaceutically conventional inorganic or organic solvents or mixtures thereof (P. List and P. C. Schmidt, Technologie pflanzlicher Arzneizubereitungen, Wissensch. Verlagsgesellschaft mbH, Stuttgart, 1984).

Conventional aqueous ethanolic extracts of Hypericum and finished pharmaceutical compositions prepared thereof usually contain less than about 1% Hyperforin (based on the extract). After the storage the value obviously decreases and moves towards zero depending on the individual storage conditions. One assumes that processes of oxidation are responsible for the degradation of the Hyperforin in the crude herbal drug and the extract.

The technical problem of the present invention is to provide improved Hyperforin-containing stabilized extracts of *Hypericum perforatum L*. (St. John's wort) in which the Hyperforin remains stable over a long period of time. It is a further technical problem of the invention to provide a process for the preparation of these stabilized extracts as well as to provide pharmaceutical compositions containing these stabilized extracts in which the Hyperforin content also remains stable.

According to the present invention these technical problems are solved by extracts according to claims 1 to 8, by the process according to claims 9 to 21 as well as by the pharmaceutical composition according to claim 22.

The present invention is based inter alia on the unexpected result that an extract of Hypericum with certain anti-oxidant and/or oxygen binding stabilizers or reducing agents, which are able to degrade oxidants such as radicals, peroxides, atmospheric oxygen etc. and/or to inhibit the degradation of Hyperforin, and optionally carrying out the extraction under inert gas such as nitrogen and/or exclusion of light and/or with a solvent with a highly reduced oxygen content, is essentially longer stable than an untreated extract of Hypericum. This extract can be derived contrary to the obsevations made by R. Berghöfer and J. Hölzl (see above) from a dried and stored crude herbal drug.

A solvent with a highly reduced oxygen content can be prepared by physical treatment such as rinsing with an inert gas such as nitrogen. In case the extract of Hypericum is preserved or stabilized according to the present invention, in particular by addition of an anti-oxidant and preferably by exclusion of light and atmospheric oxygen, then the Hyperforin in this extract remains essentially stable for a long time. The protection against light and atmospheric oxygen can also be achieved by a corresponding pharmaceutical formulation. In a preferred embodiment of the process of the present invention for the preparation of the stabilized extracts the fresh or preferably dried drug of St. John's wort is extracted with aqueous methanol or ethanol, the oxygen content of which was highly reduced by physical treatment. To the extract solution an anti-oxidant agent as a stabilizer is added and dissolved therein because of possibly present oxidants. Further examples for preferred solvents for the extraction of St. John's wort comprise the group of alkanes with low boiling points having about 5 to 8 carbon atoms such as pentanes, hexanes and heptanes, in particular n-heptane, and liquid or supercritical carbon dioxide The term "aqueous methanol or ethanol" denotes methanol or ethanol having a water content of preferably up to about 40% by volume.

Particular examples for preferred anti-oxidant stabilizers or anti-oxidant agents are pharmacologically acceptable substances, able to inhibit the degradation of Hyperforin and/or to reduce oxidants in the extract or the pharmaceutical composition. Particular examples are substances selected from the group of organic thiol compounds, such as cysteine and glutathione, as well as ascorbic acid and derivates thereof such as the fatty acid esters of ascorbic acid, such as the myristate, palmitate and stearate.

The anti-oxidant stabilizers are added to the extract solution of Hypericum in an amount sufficient to stabilize the Hyperforin. In general concentrations from 0.01 to 5% anti-oxidant stabilizer based on the extract of Hypericum are sufficient.

In a further embodiment it will be proceeded as described above but the addition of the stabilizer is carried out at the stage after drying the extract solution, i.e. after stripping off the solvent.

In a further preferred embodiment of the invention the anti-oxidant stabilizer is added, at the stage of the finished pharmaceutical product, together with other pharmaceutical additives.

Preferably all embodiments are carried out under the exclusion of light and oxygen.

The obtained extracts can be processed together with conventional pharmaceutical additives, optionally after adding again a stabilzer to pharmaceutical compositions, such as capsules, tablets and coated tablets.

Pharmaceutical additives are fillers, binding agents, disintegrants, lubricants and coating agents for film tablets and coated tablets, as well as oils and fats as fillers for soft gelatin capsules.

The present invention is explained by means of the following examples which are not intended to limit the scope of the present invention. Percentages are percents by weight if not otherwise stated. Nitrogen was used as an inert gas (protective gas). It should be noted that also other inert gases, such as argon or krypton can be used.

EXAMPLES 1a) AND 1b) (COMPARISON EXAMPLES)

a)

1 kg crude herbal drug of St. John's wort was finely milled in a mill and 7 kg 70(v/v)% ethanol was added. The suspension of 1 kg crude herbal drug and 7 kg solvent was intensively stirred at 55° C. for one hour under inert gas. Then the resulting extract was separated from the crude herbal drug by means of centrifugation. The residue of the drug was accordingly extracted for a second time with 7 kg solvent. The two extract solutions were combined and the dry residue in the extract was determined with an aliquot. The extract was gently concentrated under reduced pressure to a dry residue content of about 70% and again dried at 40° C. under reduced pressure. 0.42 kg dry extract was obtained. The Hyperforin content was 2.26% and the content of total Hypericin was 0.27%.

b)

The dry extract of Example 1a) was further processed according to the teaching of EP-A-0 599 307 by treatment with polyvinylpyrrolidon (PVP) to remove selectively Hypericines. The Hyperforin content was 2.96%.

EXAMPLE 2

24 kg crude herbal drug of St. John's wort was milled in a mill and 156 kg 80(v/v)% methanol was added, which was rinsed with nitrogen before. This mixture was then stirred for one hour at 55° C. The obtained extract solution was separated from the drug residue by means of centrifugation. The residue of the drug was accordingly extracted for a second time. The two extract solutions were combined and 1.0% by weight ascorbic acid was added. This solution was stirred for 15 minutes. Then the extract solution gently was concentrated to a dry residue content of 70% and then again dried at 40° C. under reduced pressure. 5.39 kg stabilized dry extract with a Hyperforin content of 3.2% was obtained. The content of total Hypericin in this extract was 0.48%.

EXAMPLE 3

8 kg crude herbal drug of St. John's wort was finely milled in a mill and 56 kg 70(v/v)% ethanol was added. The oxygen content of the used solvent was reduced before by means of rinsing with inert gas. The suspension of 8 kg crude herbal drug and 56 kg solvent was intensively stirred under inert gas at 55° C. for one hour. Then the obtained extract was separated from the drug by means of centrifugation while rinsing with nitrogen as an inert gas. The drug residue was extracted a second time in the same manner. The two extract solutions were combined and 0.05% L-cysteine was added. The solution was intensively stirred for 10 minutes under nitrogen as inert gas and was then gently concentrated under reduced pressure to a dry residue content of 70% and again dried at 40° C. under reduced pressure. 2.524 kg stabilized dry extract with a Hyperforin content of 3.9% was obtained. The content of total Hypericines was 0.28%.

EXAMPLE 4

454 g finely cut, fresh St. John's wort was squeezed out in a drug squeezer. 1.5 g ascorbic acid was added to the squeezed liquor (160 ml) and dissolved. The squeezed liquor was then again added to the squeezed drug. Then 1 kg n-heptan was added to the moist drug. The mixture was then extracted during one hour by permanent stirring at 50° C. under exclusion of light. Then the mixture was sucked off by means of a Seitz Supra 1500 Filter and the drug residue was extracted a second time in the same manner. The combined extract solutions were concentrated by means of a rotary evaporator at 35° C. under exclusion of light to a dry residue content of about 70% and than freeze-dried. 9.11 g dry extract was obtained with a Hyperforin content of 37.2%.

EXAMPLE 5

515 g finely cut, fresh St. John's wort was squeezed out in a drug squeezer. 1.7 g ascorbic acid was added to the squeezed liquor (180 ml) and dissolved. The squeezed liquor was than again added to the squeezed drug. Then the moist drug was delivered into a high-pressure-extraction unit and extracted under 350 bar at 40° C. with carbon dioxide. Per kg drug 20 kg carbon dioxid was used. After the extraction, the pressure was reduced to 60 bar in order to separate the extract. The extract was removed from the unit and separated from co-extracted water by means of heating to about 60° C. 12.3 g dry extract with a Hyperforin content of 43.1% was obtained.

EXAMPLE 6

Checking the Stability of Hyperforin

In this example the Hyperforin content (measured by HPLC) of an extract according to Example 1 without particular precautionary measures and additions during the preparation was compared with extracts prepared according to Examples 2 to 5 of this invention. The extracts prepared in accordance with the present invention were stored under nitrogen and exclusion of light at room temperature. The results are summarized in Table I. The result shows a substantially unchanged Hyperforin content of the extracts prepared in accordance with the present invention after 12 months. The content of total Hypericines in the extracts prepared according to Example 1 to 3 also did not change in this period of time.

TABLE I

| Dry Extract Example | Hyperforin Initial content % | Hyperforin content % |  |  |
|---|---|---|---|---|
|  |  | After 13 weeks | After 6 months | After 12 months |
| Example 1 a) | 2.26 | 0.0 | 0.0 | 0.0 |
| Example 1 b) | 2.96 | 0.0 | 0.0 | 0.0 |
| Example 2 | 3.2 | 3.2 | 3.17 | 3.15 |
| Example 3 | 3.90 | 3.90 | 3.88 | 3.85 |
| Example 4 | 37.2 | 37.2 | 36.5 | 36.1 |
| Example 5 | 43.1 | 43.1 | 43.0 | 42.4 |

EXAMPLE 7

Soft-gelatine Capsules with an Extract of Hypericum
Composition:
dry extract of Hypericum 300 mg.
ascorbic acid 0.25 mg.
octyldodecanol 200 mg
Preparation:

The extract of Examples 3 and 4 respectively, was used as dry extract. The dry extract and ascorbic acid were dispersed together in octyldodecanol and processed under exclusion of atmospheric oxygen to soft-gelatine capsules.

EXAMPLE 8

Film Tablet with Extract of Hypericum
Composition:
dry extract of Hypericum 300 mg
cellulose 100 mg
modified starch 90 mg
Na-carboxymethylcellulose 30 mg
highly dispersed siliciumdioxid 5.0 mg
ascorbic acid 5.0 mg
magnesium stearate 5.0 mg
hydroxypropylmethylcellulose-coating 20.0 mg
Preparation The extract of Example 3 was used as dry extract.

The components were mixed in dry condition in a mixer and were directly pressed into tablets. The obtained tablets were coated with a coating of hydroxypropylmethylcellulose.

EXAMPLE 9

Comparison between commercially available (German market, September 1995) finished pharmaceutical compositions of Hypericum and a finished pharmaceutical composition in accordance with the present invention.

In this example five finished pharmaceutical compositions of Hypericum, which were available on the German market in September 1995, were examined with respect of their Hyperforin content based on the extract contained in the preparation and were compared with the finished pharmaceutical composition prepared in accordance with the present invention. The results are shown in Table II. It is obvious that the pharmaceutical composition prepared in accordance with the present invention has a substantially higher Hyperforin content, which remains substantially stable even after 12 months.

TABLE II

| Composition | Parts of Hypericum extract [mg] | Contents of Hyperforin [%] |
|---|---|---|
| A | 200 | 0.58 |
| B | 250 | 0.20 |
| C | 40 | 0.07 |
| D | 110 | 0.56 |
| E | 250 | 0.71 |
| Composition prepared in accordance with the invention according to example 3 | 300 | 3.9 |

What is claimed is:

1. A stable extract of *Hypericum perforatum L.* (St. John's wort) containing Hyperforin, wherein the extract comprises an amount of a stabilizer selected from the group consisting of organic thiol compounds, ascorbic acid, ascorbic acid derivatives, and mixtures thereof effective to stabilize the Hyperforin against decomposition or degradation.

2. An extract according to claim 1, wherein the stabilizer is present in a concentration of 0.01% to 5%, based on the extract.

3. An extract according to claim 1, wherein the stabilizer is present in a concentration of 0.02% to 1%, based on the extract.

4. An extract according to claim 1, wherein the stabilizer is cysteine.

5. An extract according to claim 1, wherein the stabilizer is glutathione.

6. An extract according to claim 1, wherein the stabilizer is ascorbic acid.

7. An extract according to claim 1, wherein the stabilizer is a fatty acid ester of ascorbic acid.

8. In a process for the preparation of a stable Hyperforin-containing extract wherein *Hypericum perforatum L.* plant material is extracted with pharmaceutical inorganic or organic solvents or mixtures thereof, with the proviso that the solvents are not oily extraction agents, the improvement comprising adding a stabilizer selected from organic thiol compounds, ascorbic acid and derivatives thereof either during or after the preparation of the extract, in an amount sufficient to stabilize the Hyperforin.

9. A process according to claim 8, wherein the patent material is fresh plant material.

10. A process according to claim 8, wherein the plant material is dried plant material.

11. A process according to claim 8, wherein the stabilizer is cysteine.

12. A process according to claim 8, wherein the stabilizer is glutathione.

13. A process according to claim 8, wherein the stabilizer is asorbic acid.

14. A process according to claim 8, wherein the stabilizer is a fatty acid ester of ascorbic acid.

15. A process according to claim 8, wherein the stabilizer is added in a concentration of 0.01% to 5%, based on the extract.

16. A process according to claim 8, wherein a solvent is used for the extration, the oxygen content of which is lower or was considerably reduced.

17. A process according to claim 8, wherein the solvent used for extraction is selected from aqueous ethanol, aqueous methanol, alkanes having about 5–8 carbon atoms, liquid carbon dioxide and supercritical carbon dioxide.

18. A process according to claim 8, wherein the stabilizer is added after drying the extract solution.

19. A process according to claim 8, wherein the stabilizer is added only to the dry extract together with conventional pharmaceutical additives.

20. A process according to claim 8, wherein the process is carried out in the absence of light.

21. A pharmaceutical composition containing an extract according to claim 1 and conventional pharmaceutical additives for the treatment of depression and psychovegetative disorders.

22. The process according to claim 8, wherein the stabilizer is added in a concentration of 0.2% to 1% based on the extract.

23. The process according to claim 8, wherein the process is carried out in the absence of oxygen.

24. The process according to claim 8, wherein the process is carried out in the absence of light and oxygen.

25. A stable composition comprising
   (a) hyperforin extracted from *Hypericum perforatum L.* using water and methanol or ethanol; and
   (b) an amount of a stabilizer selected from the group consisting of organic thiol compounds, ascorbic acid, ascorbic acid derivatives, and mixtures thereof effective to stabilize the Hyperforin against decomposition or degradation.

26. A plant extract comprising
   (a) hyperforin; and
   (b) an amount of a stabilizer selected from the group consisting of organic thiol compounds, ascorbic acid, ascorbic acid derivatives, and mixtures thereof effective to stabilize the hyperforin against decomposition or degradation, the hyperforin being stable in the composition for at least 12 months.

27. A pharmaceutical composition containing an extract according to claim 1 and conventional pharmaceutical additives for the treatment of depression and psychovegetative disorders.

28. A pharmaceutical composition containing an extract according to claim 2 and conventional pharmaceutical additives for the treatment of depression and psychovegetative disorders.

29. A pharmaceutical composition containing an extract according to claim 3 and conventional pharmaceutical additives for the treatment of depression and psychovegetative disorders.

30. A pharmaceutical composition containing an extract according to claim 4 and conventional pharmaceutical additives for the treatment of depression and psychovegetative disorders.

31. A pharmaceutical composition containing an extract according to claim 5 and conventional pharmaceutical additives for the treatment of depression and psychovegetative disorders.

32. A pharmaceutical composition containing an extract according to claim 6 and conventional pharmaceutical additives for the treatment of depression and psychovegetative disorders.

33. A pharmaceutical composition containing an extract according to claim 7 and conventional pharmaceutical additives for the treatment of depression and psychovegetative disorders.

* * * * *